United States Patent [19]
Sawyer

[11] 3,956,504
[45] May 11, 1976

[54] METHOD OF PREVENTING THROMBOSES

[76] Inventor: Philip Nicholas Sawyer, 606 Third St., Brooklyn, N.Y. 11215

[22] Filed: Nov. 5, 1973

[21] Appl. No.: 412,570

Related U.S. Application Data

[63] Continuation-in-part of Ser. No. 259,271, June 2, 1972, abandoned, which is a continuation-in-part of Ser. No. 46,531, June 15, 1970.

[52] U.S. Cl. .............................................. 424/319
[51] Int. Cl.$^2$...................................... A61K 31/195
[58] Field of Search .................................... 424/319

[56] References Cited
OTHER PUBLICATIONS
Chemical Abstracts, Vol. 59, No. 15801c, (1963).

Goodman et al., The Pharmacological Basis of Therapeutics, 2nd Ed., (The Macmillan Co., N.Y.), 1955, pp. 293, 724–727, 1546, 1715 and 1716.

The Merck Index, 8th Ed., 1968, pp. 53 and 851, published by Merck and Co., Inc. N.J.

Primary Examiner—Jerome D. Goldberg

[57] ABSTRACT

In order to render the vascular system stable against the formation of thromboses, daily or periodic doses of a salt of para amino benzoic acid are taken orally or are administered by injection to give the vascular tree an internal surface charge which prevents the formation of thromboses.

4 Claims, No Drawings

METHOD OF PREVENTING THROMBOSES

OTHER APPLICATIONS

This application is a continuation-in-part of application Ser. No. 259,271 (now abandoned) filed June 2, 1972, which is a continuation-in-part of earlier filed application Ser. No. 46,531 filed June 15, 1970, and entitled ANTI-THROMBOTIC COMPOUNDS AND METHODS OF USING SAME and the disclosure of which is embodied herein. This Application also refers to and embodies the disclosure of Pat. No. 3,722,504 entitled METHOD OF SCREENING SUBSTANCES FOR USE IN THE TREATMENT OF CIRCULATORY SYSTEM DISEASES.

FIELD OF INVENTION

This invention relates to the relief and/or prevention of conditions and symptoms in the vascular tree.

DETAILED DESCRIPTION

This invention is concerned with a new use for a known pharmacologic material, namely the monovalent salts of para amino benzoic acid the potassium salt of which has been previously used in an entirely different capacity as an anti-inflammatory agent. Its structure in the potassium salt form is:

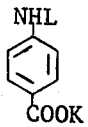

It appears that this material is useful for the relief and/or prevention of conditions and symptoms of the vascular tree and as an orally ingestible as well as an injectable material which may also be anti-atherogenic and anti-thrombotic. It has been evaluated in the electrochemical screen disclosed in Pat. No. 3,722,504. The subject material falls into group 5 of the patent application entitled ANTI-THROMBOTIC COMPOUNDS AND METHODS OF USING SAME, Ser. No. 46,531, filed June 15, 1970.

The materials more specifically put through the aforementioned electrochemical screen is potassium salt of para amino benzoic acid which is a carboxylated aminated unsaturated benzine ring.

The material was first tested with the rat mesentery technique. Control coagulation times in the rat mesentery technique are at all times around 60 minutes. Para amino benzoic acid given parenterally in various concentrations such as, for example, 0.1 mgs/100gms of rat tissue resulted in a three-time prolongation of coagulation time such as, specifically, 166.3 ± 30 minutes standard deviation, compared to an average coagulation time in the control experiment of 57 ± 10 mins. The material was initially given in concentrations of 0.1 mg/100gms tissue. Given orally (dissolved in water) in concentrations of 4mgs/100gms of tissue, the material resulted in a prolongation of thrombosis times in the rat mesentery preparation of 204 ± 46 minutes compared to a control time of 57 minutes. Para amino benzoic acid was thus shown to have a very marked effect on the rate of coagulation of vessels in the rat mesentery and on thrombosis properties.

The effect of the material on the surface charge and potential of blood vessel wall was further tested in streaming potential apparatus (see Pat. No. 3,722,504). Para amino benzoic acid was shown to increase the negative surface charge of glass in concentrations of 1, 10, and 100 milligrams per liter of streaming potential fluid (see Table 1 below). In addition, it had marked effects on streaming potential in canine carotid arteries in vitro (Table 1) increasing negative surface charge of the vessel.

Electro-osmotic determinations were carried out across both arteries and veins with various concentrations of para amino benzoic acid in the solutions. The results indicated that electro-osmotic potentials approximately doubled in both arteries and veins compared with controls.

Potassium para amino benzoic acid also increased cataphoretic (electrophoretic) mobility of red cells and white cells. There was a stoichiometric increase in the electrophoretic mobility of these cells under conditions of increasing concentrations of para amino benzoic acid, indicating that the material displays selective adsorption on erythrocyte and leukocyte membranes producing rather dramatic increases in the negative surface charge of the cell walls. The negative surface charge increased as the concentrations of the effective chemical agent increased a hundred fold from 1 milligram to 10 milligrams to 100 milligrams per liter (see Table 1).

Additional information concerning the effect of para amino benzoic acid was obtained by observing its effect on blood flow in the rat mesentery. It was shown to have rather dramatic effects increasing perfusion through capillary beds observed through the microscope as its effects increased following prolonged adsorption from intramuscular injection.

The results in the rat mesentery indicated that the potassium salt of para amino benzoic acid has predictive effects on both rat mesentery thrombosis times, blood flow through increasingly negatively charged blood vessels and probable anti-atherosclerotic as well as anti-thrombotic effects as indicated by its effect on both streaming potentials and electro-osmotic or transverse pore streaming potentials. Results of blood cell electrophoresis suggests that it effects the surface charge characteristics of erythrocytes, leukocytes, and probably on platelets acting as a dispersing agent on the cellular components of blood. Table 1 shows data relating to the effect of heparin in these same areas to show the rather dramatic correlation between potassium salt of para amino benzoic acid and heparin under many conditions. One notes that para amino benzoic acid has a more marked effect in producing increased electro-osmosis pore potentials and relatively completely correlated cellular electrophoretic effects than did heparin. However, the material is not a specific anticoagulant as is heparin — doing very little to measured clotting time and other coagulation studies in vitro (Table 2).

Because of the observed effect on rat mesentery thrombosis and the results with the other techniques of the screen, it was appropriate to evaluate the effects of the material in patients suffering from decreased limb perfusion due to advanced atherosclerosis. Since para amino benzoic acid is FDA licensed for patient use, a dosage somewhat smaller than that nominally advocated for inflammatory arthritic changes for dermatologic use was employed to determine the effects of this material on blood flow to the extremities of patients with far advanced arterial disease. The material was administered to patients as a powder in capsules. It was not certain initially that para amino benzoic acid would have effects on blood flow in this group of patients for it seemed from the electrochemical studies that its most dramatic effects would be exerted on overt thrombosis and as an anti-atherosclerotic agent.

The fact that it might have effect on blood flow as well was found by observing the rat mesentery in rats who had received intrasmuscular injections of the potassium salt of para amino benzoic acid. Here there were evidences of increased capillary bed perfusion compared to controls.

Para amino benzoic acid has been tested in 31 patients to date. It surprisingly, has been shown to increase blood flow in approximately 40% of this group of patients who had taken 0.5 to 5 and preferably 3 or 4 grams/day of the potassium salt of para amino benzoic acid orally. The advantageous affects on blood flow in these patients were measured by Doppler flow measurements as well as plethysmographic determinations of flow under highly controlled conditions of constant temperature.

It has been proven that the material has good effects on blood vessel walls, vessel wall pores, blood cells and coagulation phenomena, and is both anti-thrombotic and anti-atherogenic as indicated in the aforementioned screen.

The available evidence from human evaluation also indicates that the material tested has very definite and good effects on blood flow in maximally atherosclerotic end stage arteriosclerotic peripheral vascular disease and evidently also in coronary artery disease.

The material decreases cholesterol levels in the vast majority of patients in which these have been measured as shown in Table 2. As to patients, as appears in Table 2, it has been shown that there is in 40% (14) of the tested patients measurable improvement in blood flow, a considerable improvement, approximately 60% (16), in walking distance, a decrease in cholesterol levels, no significant change in blood sugar levels, little evidence of overt fall in blood pressure, little or no change in in vitro blood clotting time, no evidence of bleeding as indicated by the hematocrit and clinical course and some slight evidence of improvement or change in the partial thromboplastin time in a small percentage of patients specifically 5 of the patients. In approximately 60% (16) of the patients, there has been subjective improvement as established by questioning the patients in addition to their being tested.

The cumulative evidence from the material-selection electrochemical screen, including rat mesentery thrombosis evaluation, and subsequent evaluation of the material's effect on blood flow in human patients plus other measured parameters suggest that the material has some dramatic and many more pervasive effects to improve the total peripheral vascular situation in humans to whom the material is administered, which in listed tests comprised only patients with end stage arteriosclerotic peripheral vascular disease to make the testing more rigorous.

The material should be administered daily, periodically or even aperiodically in physiologically active amounts such as, for example, 0.5–5 grams (preferably 3–4 grams) per day or the equivalent thereof and preferably orally (or by injection) on a regular basis as a preventative measure against cardiac or vascular diseases.

TABLE 1

EVALUATION OF CHEMICALS IN THE ELECTROCHEMICAL SCREEN

| Material | Rat Mesentery Coagulation Time — In Min. Dose of Chemical | | | | | Streaming Potential in m.v. | | Electroosmosis potential — m.v. | Electrophoresis Zeta in m.v. Dose of Chemical | | | |
|---|---|---|---|---|---|---|---|---|---|---|---|---|
| | I.M. | | | Oral | | | Carotid | | | | | |
| | 0.1mg. | 1mg. | 10mg. | 4gm | 100gm | Glass | Artery | Artery | 1, | 10, | 100, | 1000mg/l |
| Control | 57±5 | | | | | 31±3.5 | 11 | 6.0 – 8.0 | 8 | | | |
| Heparin | 10 | 178±57 | | | | 35 to 40 | 15–20 | 9 – 15 | | 30 | 45 | .74 |
| KPABA | 163.3±31 | | | 208±57 | | 34 to 36 | 14.0 | 10.13–10.87 | 16 | 24 | 34 | |

TABLE 2

| Pt. No | Mths on drug | Patients subjective progress | Blood Flow Volume | | | Walking distance | Cholesterol | Haematocrit | Pulse Pressures | | | B. Sugar | Age | Smoking ay |
|---|---|---|---|---|---|---|---|---|---|---|---|---|---|---|
| | | | Rest blood flow | Max blood flow | Post Ex. blood flow | | | | Pop. | Tib. | Brach. | | | |
| 1 | 1½ | 0 | −1 | +2 | 0 | 300 yds 0 | — | — | — | −1 | 0 | — | 63yr | 0 |
| 2 | 10mths | +1 | 0 | R+1 L 0 | 0 | 100–250yds +1 | Fell | 0 | 0 | 0 | 0 | — | 71 | |
| 3 | 10mths | +3 | 0 | +3 | +3 | 200–∞ +3 | 0 | 0 | 0 | 0 | 0 | — | 55 | |
| 4 | | | | | | DROPPED OUT | | | | | | | 73 | |
| 5 | | | | | | " | | | | | | | 70 | |
| 6 | 8 mths | +1 | 0 | +2 | 0 | ∞ | Fell | 0 | 0 | 0 | 0 | — | 51 | |
| 7 | 3mths | 0 | +1 | 0 | +1 | 250yds 0 | Fell | 0 | −1 | 0 | 0 | — | 74 | pipe |
| 8 | 9mths | 0 | 0 | 0 | 0 | 150yds 0 | 0 | 0 | −1 | 0 | 0 | 0 | 51yrs | 1½p |
| 9 | 2 mths | +2 | 0 | +1 | +2 | | — | 0 | — | Rt 0 Lt+1 | 0 | +1 | 61yrs | 0 |
| 10 | 8 mths | +1 | 0 | −1 | +2 | 250–300 +1 | 0 | 0 | +2 | +1 | −1 | 0 | 55yrs | 1 pk |
| 11 | 8 mths | 0 | 0 | 0 | −1 | 500–400 +1 | −1 | 0 | −1 | +1 | 0 | 0 | 60yrs | 0 |
| 12 | 8mths | 0 | 0 | 0 | 0 | 0 | Fell | 0 | −1 | R−2 L+1 | 0 | 0 | 63yrs | 0 |

TABLE 2-continued

| Pt. No | Mths on drug | Patients subjective progress | Blood Flow Volume | | | Walking distance | Cholesterol | Haematocrit | Pulse Pressures | | | B. Sugar | Age | Smoking ay |
| --- | --- | --- | --- | --- | --- | --- | --- | --- | --- | --- | --- | --- | --- | --- |
| | | | Rest blood flow | Max blood flow | Post Ex. blood flow | | | | Pop. | Tib. | Brach. | | | |
| 13 | 3mths | 0 | 0 | −1 | −1 | 100−250 0 | 0 | 0 | — | −1 | −1 | 0 | 60yrs | 2pks |
| 14 | 10mths | +1 | +1 | 0 | +1 | 200−300 +1 | 0 | 0 | 0 | −1 | 0 | 0 | 73yrs | 0 |
| 15 | 7mths | +2 | 0 | +2 | +3 | 200−∞ +3 | 0 | 0 | 0 | 0 | 0 | 0 | 53yrs | 1pk |
| 16 | 4mths | +1 | 0 | 0 | Rt+1 Lt 0 | ∞ painful | 0 | 0 | 0 | 0 | 0 | −2 | 58yrs | |
| 17 | 2mths | 0 | 0 | 0 | +1 | 100−200 +1 | Fell | 0 | 0 | 0 | 0 | 0 | 53yrs | ¾pk |
| 18 | 6mths | +3 | 0 | +3 | +3 | 1mile−∞ +1 | 0 | 0 | 0 | −1 | 0 | 0 | 70yrs | pipe |
| 19 | 3mths | +1 | −1 | Rt+1 Lt 0 | 0 | 100−200 +1 | Fell | 0 | Rt+1 Lt 0 | 0 | 0 | 0 | 48yrs | |
| 20 | 6mths | +1 | 0 | 0 | 0 | 100−200 +1 ∞ | Fell | +1 | Rt−1 Lt 0 | 0 | 0 | 0 | 50yrs | cut down to 1pk |
| 21 | 5mths | +1 | −1 | −1 | −1 | 0 | Fell | +1 | 0 | 0 | 0 | 0 | 67yrs | |
| 22 | 3mths | +1 | +1 | Rt+2 Rt 0 Rt−1 | +1 | 200−300 +1 100yds | 0 | 0 | 0 | 0 | 0 | 0 | 61yrs | 2pks |
| 23 | 2mths | 0 | 0 | Lt 0 | 0 | 0 | 0 | 0 | 0 | 0 | 0 | 0 | 51yrs | 1½yr |
| 24 | | | | | | DROPPED OUT | | | | | | | | |
| 25 | 5mths | 0 | 0 | −2 | −1 | 1 mile 0 | Laboratory lost results | | −1 | 0 | 0 | — | 63yrs | 0 |
| 26 | 2mths | 0 | +1 | +1 | — | 200yds 0 | — | — | +1 | −1 | 0 | — | | |
| 27 | 1mth | 0 | −1 | −1 | ? | 200yds 0 | — | — | −1 | −1 | 0 | — | 52yrs | stopped 3yrs ag |
| *28 | 5mths | + | +1 | +2 | +1 | 100−350 +1 | 0 | 0 | +1 | +2 | 0 | Fell | | |
| *29 | 5mths | +2 | +1 | +2 | +1 | 100−300y +2 | 0 | 0 | +2 | +3 | 0 | 0 | stop | smoked 3pk/ |
| 30 | 3mths | +2 | 0 | Rt+1 Lt 0 | +2 | 200−1 mile +2 | 0 | 0 | +2 | −1 | 0 | 0 | 68yrs | nil |
| 31 | 1mth | +1 | 0 | 0 | Rt+1 Lt 0 | | 0 | 0 | 0 | +1 | 0 | 0 | 50yrs | |

GRADING
+3 Very Good
+2 Good
+1 Fair
0 No change
−1 Slightly Worse
−2 Much Worse
*Pts 28 and 29 both had aorto —femoral bipass operations, therefore it was not possible to occlude for 5 mins postoperatively....1½ mins were used.

Progress
Subjective progress ....... 16 improved
Blood flow ....... 14 actually improved
Coagulation
No change in this measurement in any patient Para amino benzoic acid has relatively little effect on coagulation phenomena so that it can be used on a chronic basis without concern about anticoagulant effects. As indicated, it has been used on patients with advanced symptomatic end stage arteriosclerotic disease involving at least the legs and frequently the brain and the coronary arteries leading to the heart. Of 35 patients selected for long term chronic evaluation using para amino benzoic acid dosages from 1–4 grams per day, 25 have completed a sufficiently long oral ingestion of para amino benzoic acid to determine whether the chemical effects the vascular tree or causes an increase in blood flow to the lower limbs.

The methods for measuring increased blood flow include strain gauge plethysmography using venous filling rate to measure the rate at which blood flows through the arterial side. Blood flows are measured in cc's/100 grams of body tissue per minute. Blood pressure at normal pulse pressure points including the femoral, popliteal, anterior tibial, and posterior tibial measuring points were determined using Doppler flow measurement techniques. Coagulation studies were carried out routinely in this group of patients as were blood chemistries for hematocrit, blood sugar, and cholesterol.

In addition to the history and physical examination as a measure of the patients arterial disease, routine arteriograms were carried out in 95% of these patients indicating in all of them the advanced stage of arteriosclerosis. Of 25 patients that completed this study, 20 were found to be improved both subjectively and objectively using multiple measurement techniques. Four were unimproved. One did not improve upon oral ingestion of PABA.

The cumulative data from this group of patients therefore indicates that para amino benzoic acid will increase blood flow to the limbs in moderately and severely advanced arteriosclerotic patients. Oral dosages range from 0.5 to 5 grams per day and produce some form of ameliorative effect of the atherosclerotic process either increasing flow through collateral vessels or opening the atherosclerotic vessels or the distal capillary beds.

The material has also been shown to decrease cholesterol levels in a large percentage of these patients. At dosages given for periods up to 15 months, the material has been shown to have essentially no effect on normal blood coagulation in patients.

What is claimed is:

1. A process for treating thromboses comprising administering to a human being in need of said treatment an anti-thromboses effective amounts of potassium salt of para amino benzoic acid.

2. A process as claimed in claim 1 wherein the salt is administered orally.

3. A process as claimed in claim 1 wherein the salt is administered in the amount of 0.5–5 grams per day.

4. A process as claimed in claim 3 wherein the salt is administered in the amount of 3–4 grams per day.

* * * * *